United States Patent
Guzowski et al.

(10) Patent No.: US 9,422,226 B2
(45) Date of Patent: Aug. 23, 2016

(54) PROCESS FOR PREPARING HIGH PURITY AND CRYSTALLINE DIMETHYL FUMARATE

(75) Inventors: John Guzowski, Melrose, MA (US); William Kiesman, Wayland, MA (US); Erwin Irdham, Melrose, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 14/124,562

(22) PCT Filed: Jun. 8, 2012

(86) PCT No.: PCT/US2012/041715
§ 371 (c)(1),
(2), (4) Date: Mar. 11, 2014

(87) PCT Pub. No.: WO2012/170923
PCT Pub. Date: Dec. 13, 2012

(65) Prior Publication Data
US 2014/0200363 A1    Jul. 17, 2014

Related U.S. Application Data

(60) Provisional application No. 61/494,775, filed on Jun. 8, 2011.

(51) Int. Cl.
| | |
|---|---|
| C07C 67/297 | (2006.01) |
| C07C 67/52 | (2006.01) |
| C07C 67/08 | (2006.01) |
| C07C 69/60 | (2006.01) |
| C07C 69/604 | (2006.01) |

(52) U.S. Cl.
CPC .............. *C07C 67/52* (2013.01); *C07C 67/08* (2013.01); *C07C 67/297* (2013.01); *C07C 69/60* (2013.01); *C07C 69/604* (2013.01); *C07B 2200/13* (2013.01)

(58) Field of Classification Search
CPC ... C07C 67/52; C07C 69/604; C07C 67/297; C07C 69/60; C07C 67/08
See application file for complete search history.

(56) References Cited

U.S. PATENT DOCUMENTS

| | | |
|---|---|---|
| 1,848,724 A | 3/1932 | Jaeger |
| 2,764,609 A | 9/1956 | Gamrath |
| 3,078,302 A * | 2/1963 | Farrar et al. ................. 560/204 |
| 3,993,684 A | 11/1976 | Dunnavant et al. |
| 4,239,636 A | 12/1980 | Brois et al. |
| 4,417,062 A | 11/1983 | Brois et al. |
| 4,568,756 A | 2/1986 | Brois et al. |
| 4,820,432 A | 4/1989 | Lundberg et al. |
| 4,827,022 A | 5/1989 | Makowka et al. |
| 4,851,439 A | 7/1989 | Speiser et al. |
| 4,866,139 A | 9/1989 | Gutierrez et al. |
| 4,866,140 A | 9/1989 | Gutierrez et al. |
| 4,866,187 A | 9/1989 | Brois et al. |
| 4,906,394 A | 3/1990 | Gutierrez et al. |
| 4,943,382 A | 7/1990 | Gutierrez et al. |
| 4,954,276 A | 9/1990 | Gutierrez et al. |
| 4,954,277 A | 9/1990 | Gutierrez et al. |
| 4,959,389 A | 9/1990 | Speiser et al. |
| 4,963,275 A | 10/1990 | Gutierrez et al. |
| 4,965,375 A | 10/1990 | Brois et al. |
| 4,971,711 A | 11/1990 | Lundberg et al. |
| 5,032,320 A | 7/1991 | Gutierrez et al. |
| 5,118,835 A | 6/1992 | Brois et al. |
| 5,153,352 A | 10/1992 | Norbeck et al. |
| 5,424,332 A | 6/1995 | Speiser et al. |
| 5,451,667 A | 9/1995 | Speiser et al. |
| 5,721,294 A | 2/1998 | Buter et al. |
| 6,100,339 A | 8/2000 | Watanabe et al. |
| 6,166,220 A | 12/2000 | Singh et al. |
| 6,204,410 B1 | 3/2001 | Kai et al. |
| 6,239,189 B1 | 5/2001 | Narayan et al. |
| 6,277,882 B1 | 8/2001 | Joshi et al. |
| 6,355,676 B1 | 3/2002 | Joshi et al. |
| 6,359,003 B1 | 3/2002 | Joshi et al. |
| 6,376,702 B1 | 4/2002 | Kai et al. |
| 6,436,992 B1 | 8/2002 | Joshi et al. |
| 6,475,697 B2 | 11/2002 | Arimoto et al. |
| 6,509,376 B1 | 1/2003 | Joshi et al. |
| 6,586,452 B1 | 7/2003 | Shih et al. |

(Continued)

FOREIGN PATENT DOCUMENTS

| | | |
|---|---|---|
| CN | 1103398 A | 6/1995 |
| CN | 102757346 A | 4/2011 |

(Continued)

OTHER PUBLICATIONS

Alzaga, R., et al., "A Generic Approach for the Determination of Residues of Alkylating Agents in Active Pharmaceutical Ingredients by In Situ Derivatization-Headspace-Gas Chromatography-Mass Spectrometry," *J. Pharm. Biomed. Anal.* 45:472-479, Elsevier Science, England (2007).

An, J., et al.,"A Practical Derivatization LC/MS Approach for Determination of Trace Level Alkyl Sulfonates and Dialkyl Sulfates Genotoxic Impurities in Drug Substances," *J. Pharm. Biomed. Anal.* 48:1006-1010, Elsevier Science, England (2008).

Chan, L.C., et al., "Selective Hydrolysis of Methanesulfonate Esters," *Org. Proc. Res. Dev.* 12(2):213-217, American Chemical Society, United States (2008).

(Continued)

*Primary Examiner* — Sudhakar Katakam
(74) *Attorney, Agent, or Firm* — Jones Day

(57) ABSTRACT

The present invention describes a process for the preparation of dimethyl fumarate. The process involves the esterification of fumaric acid and methanol in the presence of sulfuric acid as an acid catalyst. The high purity dimethyl fumarate contains no more than trace amounts of dimethyl sulfate. The present invention also provides a process for the preparation of highly pure dimethyl fumarate with a particle size from 20 to 250μm.

28 Claims, 1 Drawing Sheet

(56) References Cited

U.S. PATENT DOCUMENTS

| | | |
|---|---|---|
| 6,858,750 B2 | 2/2005 | Joshi et al. |
| 7,056,965 B2 | 6/2006 | Seyama et al. |
| 7,094,914 B2 | 8/2006 | Hibino et al. |
| 7,157,423 B2 | 1/2007 | Joshi et al. |
| 7,320,999 B2 | 1/2008 | Joshi et al. |
| 7,432,240 B2 | 10/2008 | Joshi et al. |
| 7,557,241 B2 | 7/2009 | Nakanishi et al. |
| 7,612,110 B2 | 11/2009 | Joshi et al. |
| 7,619,001 B2 | 11/2009 | Joshi et al. |
| 7,790,916 B2 | 9/2010 | Joshi et al. |
| 7,803,840 B2 | 9/2010 | Joshi et al. |
| 7,906,659 B2 | 3/2011 | Joshi et al. |
| 7,915,310 B2 | 3/2011 | Joshi et al. |
| 7,939,231 B2 | 5/2011 | Ogawa et al. |
| 8,067,467 B2 | 11/2011 | Joshi et al. |
| 8,399,514 B2 | 3/2013 | Lukashev et al. |
| 8,524,773 B2 | 9/2013 | Joshi et al. |
| 2001/0038981 A1 | 11/2001 | Arimoto et al. |
| 2002/0002306 A1 | 1/2002 | Kadowaki et al. |
| 2002/0098451 A1 | 7/2002 | Arimoto et al. |
| 2002/0183430 A1 | 12/2002 | Seyama et al. |
| 2003/0207218 A1 | 11/2003 | Sasaki et al. |
| 2004/0054001 A1 | 3/2004 | Joshi et al. |
| 2005/0085664 A1 | 4/2005 | Hibino et al. |
| 2005/0192373 A1 | 9/2005 | Awaji et al. |
| 2006/0089505 A1 | 4/2006 | Lai et al. |
| 2006/0217565 A1 | 9/2006 | Hibino et al. |
| 2007/0027076 A1 | 2/2007 | Joshi et al. |
| 2007/0173421 A1 | 7/2007 | Nakanishi et al. |
| 2008/0033199 A1 | 2/2008 | Lai et al. |
| 2008/0160449 A1 | 7/2008 | Kubo et al. |
| 2008/0233185 A1 | 9/2008 | Joshi et al. |
| 2009/0035679 A1 | 2/2009 | Ogawa et al. |
| 2009/0112016 A1 | 4/2009 | Dale et al. |
| 2009/0155866 A1 | 6/2009 | Burk et al. |
| 2009/0169677 A1 | 7/2009 | Wittorff et al. |
| 2009/0304790 A1 | 12/2009 | Nilsson et al. |
| 2010/0130607 A1 | 5/2010 | Gold |
| 2010/0305297 A1 | 12/2010 | Hoshino et al. |
| 2011/0112196 A1 | 5/2011 | Lukashev |
| 2011/0124615 A1 | 5/2011 | Joshi et al. |
| 2011/0293711 A1 | 12/2011 | Joshi et al. |
| 2012/0165404 A1 | 6/2012 | Lukashev |
| 2012/0259012 A1 | 10/2012 | Lukashev |
| 2013/0216615 A1 | 8/2013 | Goldman |
| 2013/0287732 A1 | 10/2013 | Goelz et al. |
| 2013/0295169 A1 | 11/2013 | Goldman et al. |
| 2013/0302410 A1 | 11/2013 | Gold |
| 2013/0303613 A1 | 11/2013 | Lukashev |
| 2013/0315993 A1 | 11/2013 | Nilsson et al. |
| 2013/0316003 A1 | 11/2013 | Nilsson et al. |
| 2013/0317103 A1 | 11/2013 | Lukashev |
| 2014/0037720 A1 | 2/2014 | Nilsson et al. |
| 2014/0037740 A1 | 2/2014 | Nilsson et al. |
| 2014/0066505 A1 | 3/2014 | Joshi et al. |
| 2014/0099364 A2 | 4/2014 | Nilsson et al. |
| 2014/0163100 A1 | 6/2014 | Dawson et al. |
| 2014/0179779 A1 | 6/2014 | Chao |

FOREIGN PATENT DOCUMENTS

| | | |
|---|---|---|
| CN | 102432464 A | 12/2011 |
| CN | 102766050 A | 8/2012 |
| CN | 103848739 A | 3/2014 |
| EP | 1176136 A1 | 1/2002 |
| EP | 2 379 063 B1 | 3/2013 |
| JP | 60-193946 | 10/1985 |
| JP | 61-246147 | 11/1986 |
| JP | 2537955 B2 | 9/1996 |
| JP | 2003-160535 | 6/2003 |
| JP | 2004-10530 | 1/2004 |
| KR | 1020010112941 | 12/2001 |
| WO | WO 98/44007 A1 | 10/1998 |
| WO | WO 99/25678 A1 | 5/1999 |
| WO | WO 2006/037342 A2 | 4/2006 |
| WO | WO 2006/050730 A1 | 5/2006 |
| WO | WO 2006/114900 A1 | 11/2006 |
| WO | WO 2007/006307 A2 | 1/2007 |
| WO | WO 2007/042034 A1 | 4/2007 |
| WO | WO 2007/042035 A2 | 4/2007 |
| WO | WO 2007/087815 A2 | 8/2007 |
| WO | WO 2009/045637 A2 | 4/2009 |
| WO | WO 2010/079222 A1 | 7/2010 |
| WO | WO 2011/017543 A1 | 2/2011 |

OTHER PUBLICATIONS

Friedli, F.E., "Rate of Quaternization as a Function of the Alkylating Agent," *Proc. World Conf. Oleochem. Into the 21$^{st}$ Century*, 296-297, American Oil Chemist's Society, United States (1991).

Hoffmann, G.R., "Genetic Effects of Dimethyl Sulfate, Diethyl Sulfate, and Related Compounds," *Mutation Research* 75:63-129, Elsevier, Netherlands (1980).

Holland, P., and White, R.G., "Cutaneous Reactions Produced by Fumaronitrile in Human Subjects," *Brit. J. Dermatol.* 85(3):259-263, Blackwell Scientific Publications, England (1971).

Kolensikov, V.A., *Kinetika I Katliz* 18:1065-1066 (1977).

Kooijman, H., et al., "Dimethyl fumarate," *Acta Crystallographica Section E: Structure Reports Online* E60:o917-o918, International Union of Crystallography, Great Britain (2004).

Kuroda, K., et al., "Inhibitory Effect of Capsella bursa-pastoris Extract on Growth of Ehrlich Solid Tumor in Mice," *Cancer Res.* 36(6):1900-1903, American Association for Cancer Research, United States (1976).

Robinson, D.I., "Control of Genotoxic Impurities in Active Pharmaceutical Ingredients: A Review and Perspective," *Org. Proc. Res. Dev.* 14(4):946-959, American Chemical Society, United States (2010).

Schilling, S., et al., "Fumaric Acid Esters are Effective in Chronic Experimental Autoimmune Encephalomyelitis and Suppress Macrophage Infiltration," *Clin. Exp. Immunol.* 145:101-107, British Society for Immunology, Great Britain (2006).

Sheldrick, G.M., "A Short History of SHELX," *Acta Cryst. Section A: Foundations of Crystallography* A64:112-122, International Union of Crystallography, Singapore (2008).

Staples, R.J. and Gingold, J.A., "Crystal structure of isopropyl-N-(3-chlorophenyl)carbamate, $C_{10}H_{12}ClNO_2$, Chloropropham," *Z. Kristallogr. NCS* 224:121-123, Oldenbourg Wissenschaftsverlag, Germany (2009).

Tan, E-L., "Mutagenicity and Cytotoxicity of Dimethyl and Monomethyl Sulfates in the CHO/HGPRT System," *Journal of Toxicology and Environmental Health* 11(3):373-380, Taylor & Francis, United States (1983).

Teasdale, A., et al., "A Detailed Study of Sulfonate Ester Formation and Solvolysis Reaction Rates and Application toward Establishing Sulfonate Ester Control in Pharmaceutical Manufacturing Processes," *Org. Proc. Res. Dev.* 14(4):999-1007, American Chemical Society, United States (2010).

Thayer, F.K., "Methylethyl Sulfate as in Alkylating Agent," *J. Am. Chem. Soc.* 46:1044-1046, American Chemical Society, United States (1924).

Wolfenden, R. and Yuan, Y., "Monoalkyl sulfates as alkylating agents in water, alkylsulfatase rate enhancements, and the "energy-rich" nature of sulfate half-esters," *P.N.A.S. USA* 104:83-86, National Academy of Sciences, United States (2007, Epub 2006).

Zheng, J., et al., "Determination of low ppm levels of dimethyl sulfate in an aqueous soluble API intermediate using liquid-liquid extraction and GC-MS," *J. Pharm. Biomed. Anal.* 50(5):1054-1059, Elsevier Science, England (2009).

U.S. Appl. No. 13/578,430, inventors Goelz et al., international filing date Feb. 11, 2011(Abandoned).

U.S. Appl. No. 14/119,373, inventors Dawson, K., et al., § 371(c) date Feb. 18, 2014, published as US 2014/0163100 A1 on Jun. 12, 2014.

U.S. Appl. No. 14/136,990, inventor Jianhua Chao, filed Dec. 20, 2013, published as US 2014/0179779 A1 on Jun. 26, 2014.

U.S. Appl. No. 14/201,380, inventor Jianhua Chao, filed Mar. 7, 2014 (Not Published).

(56) References Cited

OTHER PUBLICATIONS

U.S. Appl. No. 14/264,653, inventor Ralf Gold, filed Apr. 29, 2014 (Not Published).
International Search Report for International Patent Application No. PCT/US12/41715, International Searching Authority, United States, mailed on Aug. 28, 2012.
Sobol, Z., et al., "Genotoxicity profiles of common alkyl halides and esters with alkylating activity," *Mutat. Res. 633*:80-94, Elsevier B.V., Netherlands (2007).
Teasdale, A., et al., "Mechanism and Processing Parameters Affecting the Formulation of Methyl Methanosulfonate from Methanol and Methanesulfonic Acid:An Illustrative Example for Sulfonate Ester Impurity Formation," *Org. Proc. Res. Dev. 13*(3):429-433, Organic Process Research & Development, American Chemical Society, United States (2009).
"Dimethyl sulfate," *IARC Monographs on the Evaluation of Carcinogenic Risks to Humans: Re-evaluation of Some Organic Chemicals, Hydrazine and Hydrogen Peroxide 71*:575-588, World Health Organization: International Agency for Research on Cancer, Lyon, France (1999).
U.S. Appl. No. 13/955,580, filed Jul. 31, 2013 (Abandoned).
U.S. Appl. No. 13/957,063, filed Aug. 1, 2013 (Abandoned).
U.S. Appl. No. 13/957,295, filed Aug. 1, 2013 (Abandoned).
U.S. Appl. No. 14/209,480, filed Mar. 13, 2014 (Not Published).
U.S. Appl. No. 14/209,584, filed Mar. 13, 2014 (Not Published).
U.S. Appl. No. 14/209,651, filed Mar. 13, 2014 (Not Published).
U.S. Appl. No. 14/209,712, filed Mar. 13, 2014 (Not Published).
U.S. Appl. No. 14/209,756, filed Mar. 13, 2014 (Not Published).
U.S. Appl. No. 14/209,823, filed Mar. 13, 2014 (Not Published).
U.S. Appl. No. 14/212,503, filed Mar. 14, 2014 (Not Published).
U.S. Appl. No. 14/212,685, filed Mar. 14, 2014 (Not Published).
U.S. Appl. No. 14/213,321, filed Mar. 14, 2014 (Not Published).
U.S. Appl. No. 14/213,399, filed Mar. 14, 2014 (Not Published).
U.S. Appl. No. 14/213,673, filed Mar. 14, 2014 (Not Published).
Prior Art Search Report issued by the WIPS Co. Ltd. and received by the Korean Intellectual Property Office on Sep. 25, 2014 in connection with Korean Patent Application No. 2014-7000390 (English translation).
Cao, "Synthesis of Dimethyl Fumarate from Cis-butenedioic Acid," *Chemical Industry and Engineering Progress*, 4th Issue, pp. 33-34 and 39 (2001) (with English concise explanation of relevance).
Xiang, "Progress in Synthesis of Dimethyl Fumarate," *Advances in Fine Petrochemicals*, vol. 8, issue 5, pp. 32-36 (May 2007) (with English Abstract).
Li and Liu, "Synthesis of dimethylfumarate by Nd2O3 catalysis," *Specialty Petrochemicals*, Apr. 1997, http://en.cnki.com.cn/Article_en/CJFDTOTAL-JXSY199704009.htm (with English Abstract).
Opposition to Ecuadorian Application No. SP 2014-13123, Submission by ALAFAR, 2015 (with English translation).
Lin et al., "The Anti-Inflammatory Effects of Dimethyl Fumarate in Astrocytes Involve Glutathione and Haem Oxygenase-1," *ASN Neuro* 2011 3: DOI: 10.1042/AN20100033, http://asn.sagepub.com/content/3/2/AN20100033.
Vandermeeren et al., "Dimethylfumarate is an Inhibitor of Cytokine-Induced Nuclear Translocation of NF-κB1, but not RelA in Normal Human Dermal Fibroblast Cells," *Journal of Investigative Dermatology* (2001) 116, 124-130.
Loewe et al., "Dimethylfumarate Inhibits TNF-Induced Nuclear Entry of NF-κB/p65 in Human Endothelial Cells," *J Immunol*. May 1, 2002;168(9):4781-7.
Linker et al., "Fumaric acid esters exert neuroprotective effects in neuroinflammation via activation of the Nrf2 antioxidant pathway," *Brain*. Mar. 2011; 134 (Pt 3):678-92.
Remington's Pharmaceutical Sciences, 1980, 16th Edition, Mack Publishing Company, Easton, PA, pp. 180-181.
Giron, "Thermal analysis and calorimetric methods in the characterization of polymorphs and solvates," *Thermochimica Acta* 248 (1995) pp. 1-59.
Garrido, "Form and Structure of Crystals," Alhambra Editorial, Mexico, Chapter V: Crystalline Forms Characteristics, 1973, pp. 204-225 (with English translation).
Lei et al., "Novel technology of dimethyl fumarate synthesis," *Resource Development & Market* (2011) 27(9) (English translation of abstract).
Qu et al., "Study on synthesis of dimethy (sic) fumarate with mixed heteropoly acid catalyst," *Journal of Northeast Normal University* (Natural Science Edition), 2011-02, http://en.ciki.com.cn/Article_en/CJFDTOTAL-DBSZ201102021.htm (with English Abstract).
Carr, "Bioactive Marine Natural Products Isolation, Structure Elucidation and Synthesis of Pharmacophore Analogues," PhD Thesis, The University of British Columbia (Mar. 2010) http://hdl.handle.net/2429/23166.
Zhao et al., "Alkyl sulfonate functionalized ionic liquids: synthesis, properties, and their application in esterification," *Chin. J. Catal.* (2011) 32:440-445.
Tachibana et al., "Synthesis of biomass-based monomers from biomass-based furfural for polyesters and evaluation of their biomass carbon ratios," in Biobased Monomers, Polymers, and Materials; Smith, P. et al.; ACS Symposium Series; American Chemical Society: Washington, DC, 2012: Chapter 7, pp. 91-110.
Ivanova et al., "Effect of imidazolium salts on the catalytic reaction of 1,3-dioxolanes with methyl diazoacetate," *Russian Journal of General Chemistry* (2011) 81(1):106-108.
Enthaler et al., "Highly Selective Iron-Catalyzed Synthesis of Alkenes by the Reduction of Alkynes," *Chem. Asian J.* (2011) 6:1613-1623.
Booth et al., "Regulation of dimethyl-fumarate toxicity by proteasome inhibitors," *Cancer Biology & Therapy* (2014) 15:12, 1646-1657.
Thomson et al., "Case Studies in the Applicability of Drug Substance Design Spaces Developed on the Laboratory Scale to Commercial Manufacturing," *Org. Process Res. Dev.* (2014), dx.doi.org/10.1021/op500187u.
Extended European Search Report for Application No. EP 12796164.7, issued Jul. 10, 2015.
Radell et al., "Effect of cis-trans isomerism on the urea inclusion compound forming ability of a molecule; study of the maleate-fumarate system," *J. Org. Chem.* (1961) 26(8):2960-2963.
Ma, "Synthesis of dimethyl fumarate," XP002735800, retrieved from STN Database accession No. 2006:723997 (2006).
Wei et al., "Synthesis of dimethyl fumarate," XP002735801, retrieved from STN Database accession No. 1998:355979 (1998).
Huang et al., "Synthesis of dimethyl fumarate," XP002735802, retrieved from STN Database accession No. 1989:514725 (1989).
Guzowski et al., "Understanding and Control of Dimethyl Sulfate in a Manufacturing Process: Kinetic Modeling of a Fischer Esterification Catalyzed by $H_2SO_4$," *Org. Process Res. Dev.*, 2012 (published Dec. 23, 2011), 16:232-239; dx.doi.org/10.1021/op200323j.
Li and Liu, "Synthesis of dimethylfumarate by Nd2O3 catalysis," *Specialty Chemicals*, 1997-04, http://en.cnki.com.cn/Article_en/CJFDTOTAL-JXSY199704009.htm (with full English translation).
Shi and Wang, "Research on Synthesis of Dimethyl Fumarate," *Specialty Chemicals*, 1990-07, doi:10.13550/j.jxhg.1990.06.005 (with full English translation).
Ma, "Research on Synthesis of Dimethyl Fumarate," *Chemical Industry Times* (2005) 19(4):18-19.
Wei, et al., "Research on Synthesis of Dimethyl Fumarate," *Guangxi Chemical Industry* (1998) 27(1):27-29, 32.
Huang, et al., "Synthesis of Dimethyl Fumarate," *Chemical World* (1989) 30(3) 102-104.

\* cited by examiner

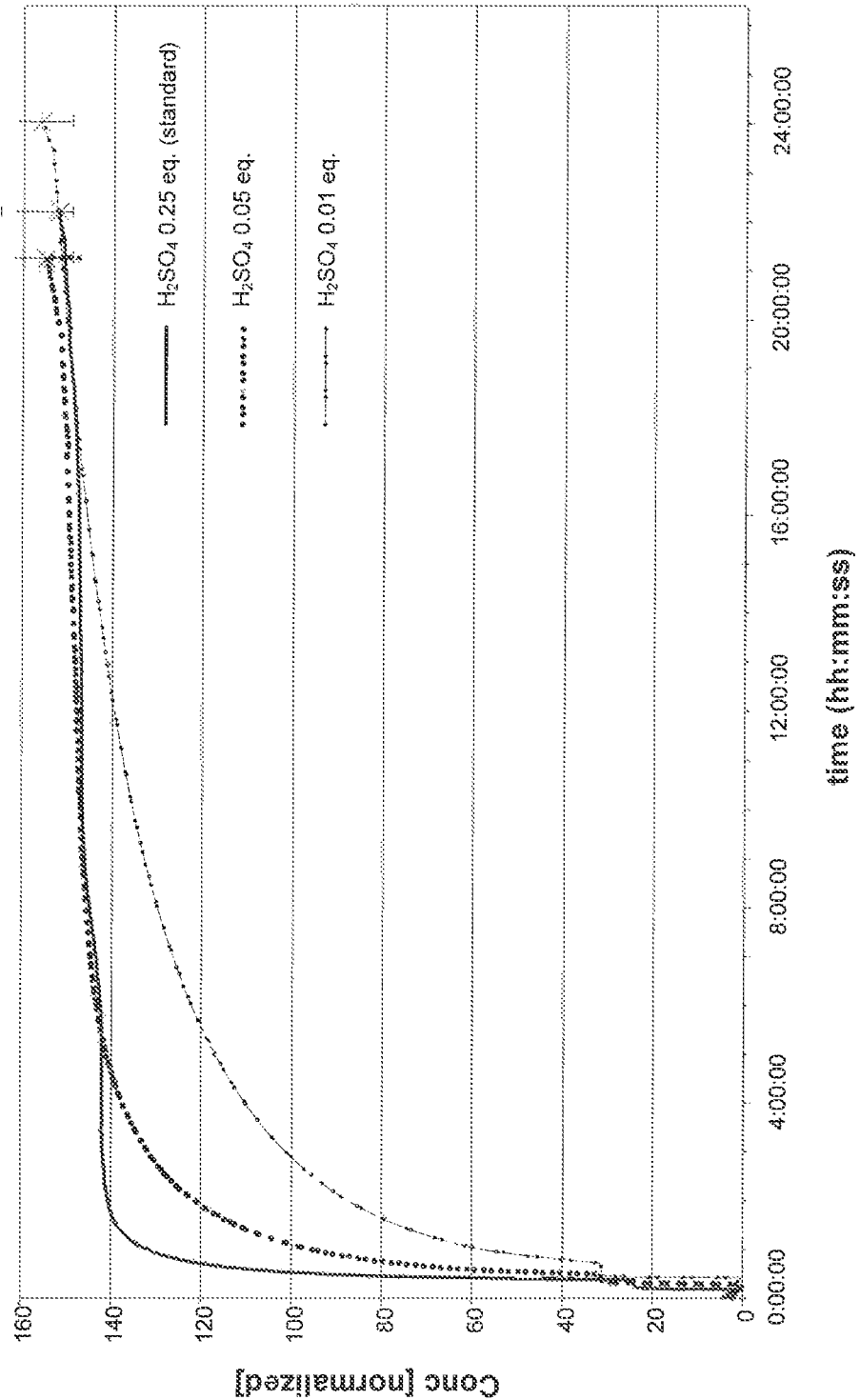

PROCESS FOR PREPARING HIGH PURITY AND CRYSTALLINE DIMETHYL FUMARATE

BRIEF SUMMARY OF THE INVENTION

The methods provided are exemplary and are not intended to limit the scope of the claimed embodiments.

In one embodiment, the present invention provides a method for preparing dimethyl fumarate, which comprises: reacting:
(a) fumaric acid; and
(b) methanol;
(c) in the presence of sulfuric acid;
in a reaction mixture to obtain a product mixture comprising a low level of dimethyl sulfate.

In one embodiment, the level of dimethyl sulfate in the product mixture is less than 4.0 ppm. In another embodiment, the level of dimethyl sulfate in the product mixture is less than 3.0 ppm. In another embodiment, the level of dimethyl sulfate in the product mixture is less than 2.0 ppm. In another embodiment, the level of dimethyl sulfate in the product mixture is less than 1.0 ppm.

In one embodiment, the present invention provides a method for preparing dimethyl fumarate, which comprises:
(1) reacting:
(a) fumaric acid; and
(b) methanol;
(c) in the presence of sulfuric acid;
in a reaction mixture to obtain a product mixture comprising a low level of dimethyl sulfate; and
(2) reducing the particle size of the dimethyl fumarate.

In one embodiment, the particle size of dimethyl fumarate ranges from about 20 μm to about 250 μm.

In one embodiment, the present invention provides a method for the preparation of dimethyl fumarate of crystal form I, wherein the crystal form is characterized by peaks expressed in degrees 2θ at approximately 10.96 and 22.01, which comprises:
reacting:
(a) fumaric acid; and
(b) methanol;
(c) in the presence of sulfuric acid;
in a reaction mixture to obtain a product mixture comprising a low level of dimethyl sulfate.

In one embodiment, the crystal form is further characterized by peaks expressed in degrees 2θ at approximately 24.07, 24.11, 24.17, and 27.39.

In one embodiment, the method further comprises: recrystallizing the dimethyl fumarate using an organic solvent.

In one embodiment, the organic solvent is selected from the group consisting of acetone, anisole, benzyl alcohol, 1-butanol, 2-butanol, cumene, dichloromethane, diethyl ether, 1,4-dioxane, N,N-dimethylformamide (DMF), dimethyl sulfoxide (DMSO), ethyl acetate (EtOAc), ethanol, ethylene glycol, ethyl formate, water, heptane, isobutyl acetate, isopropyl ether, isopropyl acetate, isooctane, acetonitrile, methyl ethyl ketone, methanol, methyl acetate, methylcyclohexane, methyl isobutyl ketone, nitrobenzene, N-methylpyrrolidone (NMP), 1-octanol, isopentanol, propyl acetate, 1-propanol, 2-propanol, pyridine, t-butyl methyl ether (TBME), tetrahydrofuran (THF), triethylamine, trifluorotoluene, toluene, p-xylene, and mixtures thereof.

In one embodiment, the present invention provides dimethyl fumarate which is prepared by a method of the present invention.

In one embodiment, the present invention provides crystal form I of dimethyl fumarate which is prepared by a method of the present invention.

A pharmaceutical composition comprising dimethyl fumarate wherein the particle size of dimethyl fumarate ranges from about 20 μm to about 250 μm.

BRIEF DESCRIPTION OF THE DRAWING

FIG. 1 provides the kinetic and equilibrium formation of dimethyl fumarate under varying sulfuric acid amounts at 65° C.

DETAILED DESCRIPTION OF THE INVENTION

The present invention provides a process for the preparation of highly pure dimethyl fumarate by esterifying fumaric acid and methanol in the presence of sulfuric acid as an acid catalyst and water sequestrant. It has been discovered that this process produces high purity dimethyl fumarate containing no more than trace amounts of dimethyl sulfate.

The present invention also provides a process for the preparation of highly pure dimethyl fumarate with a particle size from 20 to 250 μm. The process of the invention provides dimethyl fumarate having a particle size wherein at least 97% of the particles have a particle size of less than 250 μm.

Fumaric acid is an intermediate in the citric acid cycle that is hydrated by the enzyme fumarase to maleic acid. The use of fumaric acid for the treatment of psoriasis was introduced in 1959. Fumaric acid has also been shown to impede the growth of Ehrlich solid tumor cells in mice. Kuroda, K., et al., *Cancer Res.* 36:1900-1903 (1976).

Previously known salts and derivatives of fumaric acid were not resorbed, or only insufficiently resorbed, due to their relatively strong polar hydrophilic character, during their short residence time on lipophilic organ boundary layers. For this reason, high doses have been used, which resulted in side effects including headaches, eructation, dizziness, nausea, vomiting, abdominal and intestinal cramps, diarrhea, and flushing. High doses of fumaric acid, its salts, and derivatives such as dihydroxy fumaric acid, fumaramide, and fumaronitrile had such an unacceptable rate of side effects and high toxicity that it was necessary to refrain from such therapy. See P. Holland, et al., *Brit. J. Dermatol.* 85:259-263 (1971).

In the 1980's, more standardized oral preparations of fumaric acid esters were developed, containing dimethylfumarate and monoethyl fumarate as the main components. After oral uptake, dimethyl fumarate is rapidly hydrolyzed to methyl hydrogen fumarate. The biological half-life of methyl hydrogen fumarate is 36 hours with 30% being bound by serum proteins. Schilling, S., et al., *Clin. Exp. Immunol.* 145:101-107 (2006).

U.S. Pat. No. 4,851,439 discloses fumaric acid derivatives in the form of pro-drugs. U.S. Pat. No. 4,959,389 discloses pharmaceutical compositions including at least one salt of fumaric acid monoalkyl ester for the treatment of psoriasis and psoriatic arthritis. U.S. Pat. No. 5,424,332 discloses calcium, magnesium, zinc, and iron salts of fumaric acid monoalkyl esters. U.S. Pat. No. 5,451,667 discloses derivatives of fumaric acid of the formula:

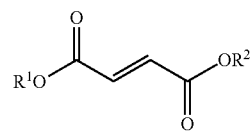

wherein:
R$^1$ is a hydrogen atom, a C$_{1-8}$ alkyl group, or a metallic cation such as, for example, Na, Ca, or Zn; and
R$^2$ is a saturated or unsaturated aliphatic C$_{6-24}$ alkyl group, psoralen-9-yl, retinyl, α-tocopheryl, calciferyl, corticosteroid-21-yl, or monosaccharid-ω-yl,
for the treatment of cryptogenically-caused diseases. U.S. Pat. No. 6,277,882 discloses the use of alkyl hydrogen fumarates for preparing compositions for treating psoriasis, psoriatic arthritis, neurodermatitis, and enteritis regionalis Crohn. U.S. Pat. No. 6,355,676 discloses the use of salts of fumaric acid monoalkyl esters optionally in admixture with a dialkyl fumarate for the treatment of psoriatic arthritis, neurodermatitis, psoriasis, and enteritis regionalis Crohn. U.S. Pat. No. 6,359,003 discloses the use of fumaric acid monoalkyl esters for transplantation medicine. U.S. Pat. No. 6,858,750 discloses the use of pharmaceutical compositions of fumaric acid derivatives for the treatment of mitochondrial diseases. U.S. Pat. No. 7,320,999 discloses the use of dialkyl fumarates for the therapy of autoimmune diseases.

There is significant interest in the manufacture and regulation of pharmaceuticals regarding the generation and analysis of genotoxic impurities. U.S. Patent Appl. No. 2009/0112016 discloses the use of sulfonated resin catalysts in esterification reactions to reduce by-product formation. The inventors disclose that the catalyst is useful for any catalyzed esterification process that suffers from deleterious side reactions, with fumaric acid being a preferred organic acid of the invention (page 6, paragraph [0073]).

U.S. Patent Appl. No. 2002/0002306 discloses a method of producing dimethyl fumarate containing no catalyst residue by use of a heterogenous Group VIII catalyst which is readily separable and non-corrosive. The inventors state that isomerization of a maleate with an acid such as concentrated sulfuric acid can corrode the reaction vessel and the remaining sulfate ions can adversely affect curing (page 1, paragraph [0006]).

Accordingly, there is a need in the art to provide a scalable industrial process for synthesizing highly pure dimethyl fumarate that contains no more than trace amounts of dimethyl sulfate.

Additionally, there is a need in the art to provide a scalable industrial process for synthesizing highly pure dimethyl fumarate crystal form I that contains no more than trace amounts of dimethyl sulfate.

The process of the present invention includes, in various embodiments, reacting fumaric acid or a salt thereof with methanol, with or without a co-solvent, in the presence of sulfuric acid.

formation of one equivalent of water. The esterification reaction is reversible and, under defined conditions, the reaction will reach an equilibrium. The equilibrium will be shifted toward the product by, for example, increasing the methanol concentration and/or removing water from the reaction mixture. However, increasing the water concentration during the reaction will result in shifting the equilibrium back toward the starting material and result in partial ester hydrolysis.

The esterification reaction creating dimethyl fumarate reaches equilibrium between methyl hydrogen fumarate and the product, dimethyl fumarate. The reaction, which is initially heterogeneous, due to limited fumaric acid solubility in methanol, gradually becomes a homogenous reaction upon heating to the reaction temperature (reflux at 60-70° C.).

Methyl hydrogen fumarate (MHF) is formed rather quickly from the starting material, fumaric acid. The time required to reach the equilibrium level for MHF and the product dimethyl fumarate, depends on the amount of sulfuric acid (catalyst) used. These results are illustrated in FIG. 1 for reaction with different amounts of sulfuric acid catalyst (0.01, 0.05 and 0.25 mol. equivalent). These reactions gave dimethyl fumarate in similar isolated yields (78-79%) with no detectable methyl hydrogen fumarate. The reaction profiles suggest that equilibrium concentrations of product were achieved at all levels of sulfuric acid catalyst used if the reaction was held for a sufficiently long period of time.

The term "about" is used herein to mean the given number plus or minus 1 to 10%.

An excess amount of methanol is typically used in the reaction. In one embodiment, the fumaric acid and methanol can be added together in a ratio of from about 2.0 to about 10.0, about 2.0 to about 9.0, about 2.0 to about 8.0, about 2.0 to about 7.0, about 2.0 to about 6.0, about 3.0 to about 10.0, about 3.0 to about 9.0, about 3.0 to about 8.0, about 4.0 to about 10.0, about 4.0 to about 9.0, about 4.0 to about 8.0, about 5.0 to about 8.0, or about 5.7 to about 8.6 liters of methanol per kilogram of fumaric acid. In another embodiment, the ratio of methanol to fumaric acid is about 6.0 liters per kilogram, about 6.5 liters per kilogram, about 7.0 liters per kilogram, about 7.5 liters per kilogram, about 8.0 liters per kilogram, or about 8.5 liters per kilogram. In another embodiment, the ratio of methanol to fumaric acid is about 5.77 liters per kilogram to about 5.87 liters per kilogram. In one embodiment, the fumaric acid and methanol can be added together in a ratio of from about 500 to about 1000, about 500 to about 900, about 500 to about 800, about 600 to about 1000, about 600 to about 900, about 600 to about Scheme 1

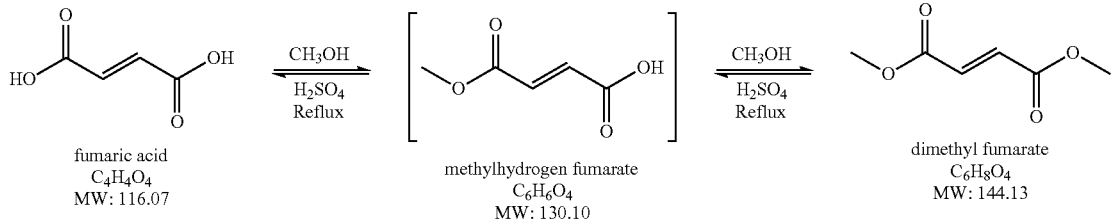

The esterification of dimethyl fumarate is illustrated in Scheme 1. The first step, proton transfer, occurs very rapidly and is, under the reaction conditions, irreversible. The second step, esterification with methanol, occurs under the 800, about 700 to about 800, or about 740 to about 742 kilograms of methanol per kilogram of fumaric acid.

Increasing the water concentration during the reaction will result in shifting the equilibrium back toward the starting material and result in partial ester hydrolysis. Therefore, it is desirable to keep the amount of water added to the reaction mixture low. In one embodiment, the amount of water in the starting reaction materials is from about 0.5 to about 6.0%, about 0.5 to about 5.5%, about 1.0 to about 6.0%, about 1.0 to about 5.0%, about 1.0 to about 4.0%, about 2.0 to about 5.0%, about 2.0 to about 4.0%, or about 2.0 to about 3.0%. In one embodiment, the amount of water in the fumaric acid added to the reaction mixture is less than 0.5%. In one embodiment, the methanol is anhydrous. In one embodiment, the amount of water in the methanol added to the reaction mixture is from about 0 to about 1%, about 0 to about 0.5%, or about 0.5 to about 1.0%. In another embodiment, the amount of water in the methanol added to the reaction mixture is less than 0.5%. In one embodiment, the amount of water in the methanol added to the reaction mixture is from about 0 to about 1%, about 1 to about 0.5%, or about 0.1 to about 0.5%. In another embodiment, the amount of water in the methanol added to the reaction mixture is less than 0.1%.

The acid catalyst is employed in an amount sufficient to catalyze the reaction. The acid catalyst can also serve as a dehydrating agent or desiccant for water produced as a by-product of the reaction. In one embodiment the acid catalyst is sulfuric acid. In one embodiment, the fumaric acid and acid catalyst are added together in a ratio of fumaric acid:acid catalyst in a range of from about 1:0.01 to about 1:0.50 or about 1:0.238 to about 1:0.243 molar equivalents. In another embodiment, the ratio of fumaric acid:acid catalyst is about 1:0.01, 1:0.10, 1:0.20, 1:0.30, 1:0.40, or 1:0.50 molar equivalents.

In some embodiments, the reaction mixture can include an additional non-reactive co-solvent that does not chemically interfere with the reaction. Non-limiting examples of non-reactive co-solvents include methyl acetate, ethyl acetate, isopropyl acetate, n-butyl acetate, isobutyl acetate, acetone, methyl ethyl ketone, methyl isobutyl ketone, tetrahydrofuran, 2-methyltetrahydrofuran, acetonitrile, methyl t-butyl ether, dibutyl ether, cyclopentyl methyl ether, anisole, toluene, xylene, heptanes, and mixtures thereof. In one embodiment, the ion-reactive co-solvents include methyl acetate, ethyl acetate, isopropyl acetate, n-butyl acetate, isobutyl acetate, acetone, methyl ethyl ketone, methyl isobutyl ketone, dibutyl ether, anisole, toluene, heptanes, and mixtures thereof.

Higher reaction temperatures are preferred to improve the solubility of the fumaric acid in methanol and to improve the rate of the reaction. Water is produced as a byproduct during the esterification reaction. Analysis shows water increased from 2% at the beginning of the reaction to 5% at the end of reaction. A consistent yield can be achieved by allowing sufficient time (normally within 3 hours) for the reacting system to reach an equilibrium state. In one embodiment, the reaction conditions include reacting at a temperature of from about 55° C. to about 75° C., about 60° C. to about 75° C., about 65° C. to about 75° C., about 70° C. to about 75° C., about 60° C. to about 75° C., or about 60° C. to about 70° C. In another embodiment, the reaction temperature for the esterification is about 60° C. In another embodiment, the reaction temperature for the esterification is about 70° C.

The reaction can proceed for any length of time necessary to achieve conversion of fumaric acid to dimethyl fumarate. In one embodiment, the reaction proceeds for about 1.5 to about 48 hours. In another embodiment, the reaction proceeds for about 3.0 to about 27 hours. In another embodiment, the reaction proceeds for about 1.5 to about 27 hours. In another embodiment, the reaction proceeds for about 3.0 to about 48 hours.

Following the esterification process, dimethyl fumarate can be crystallized from the reaction mixture by conventional methods known to those in the art. In one embodiment, the hot mixture of dimethyl fumarate is filtered through a filter media. In one embodiment, the hot mixture of dimethyl fumarate is cooled to a temperature of from about 0° C. to about 30° C., about 10° C. to about 30° C., about 15° C. to about 30° C., about 20° C. to about 30° C., about 0° C. to about 25° C., or about 10° C. to about 25° C. In another embodiment, the hot mixture of dimethyl fumarate is cooled to a temperature of less than 25° C. In one embodiment, the hot product mixture is cooled down over from about 7 to about 10 hours, about 8 to about 10 hours, about 9 to about 10 hours, about 7 to about 9 hours, or about 8 to about 9 hours. Cooling the product mixture allows the dimethyl fumarate to crystallize out of the solution and methyl hydrogen fumarate remains in the solution. In one embodiment, the cooled product mixture is stirred for about 0.5 to about 5 hours, about 1 to about 5 hours, about 2 to about 5 hours, about 3 to about 5 hours, about 1 to about 4 hours, about 1 to about 3 hours, or about 1 to about 2 hours.

Following the crystallization process, the dimethyl fumarate can be isolated from the reaction mixture by conventional methods known to those in the art. In one embodiment, the product is isolated using a centrifuge. After isolation, the product can be washed with an organic solvent. In one embodiment, the product is washed with methanol. In one embodiment, the product is washed with about 0.1 to about 6.0, about 0.1 to about 5.0, about 0.1 to about 4.0, about 0.1 to about 3.0, about 0.1 to about 1.5, about 0.5 to about 6.0, about 0.5 to about 5.0, about 1.0 to about 6.0, about 1.0 to about 5.0, about 1.5 to about 6.0, about 1.5 to about 5.5, about 0.3 to about 0.7, about 0.3 to about 0.6, about 0.4 to about 0.9, about 0.4 to about 0.8, about 0.5 to about 0.8, about 0.6 to about 0.8, or about 0.66 to about 6.49 kilograms of methanol per kilogram of product. In another embodiment, the product is washed with about 1.44 to about 5.75 kilograms of methanol per kilogram of product.

Following the isolation process, the dimethyl fumarate can be dried using conventional methods known in the art. The extent of drying of the dimethyl fumarate depends on time, temperature, and to some extent the type and capacity of the dryer. Dimethyl fumarate has a low measurable vapor pressure. Therefore, placing the material under reduced pressure in a dryer could potentially promote sublimation and subsequent particle size changes. In one embodiment, the dimethyl fumarate is dried at a temperature of about 10 to about 50° C., about 20 to about 50° C., about 10 to about 40° C., about 20 to about 40° C., or about 10 to about 50° C. In another embodiment, the dimethyl fumarate is dried at a temperature of about 23 to about 27° C. In one embodiment, the dimethyl fumarate is dried at a pressure of about 10 to about 200 mbar, about 20 to about 200 mbar, about 30 to about 200 mbar, about 20 to about 100 mbar, about 40 to about 100 mbar, or about 30 to about 100 mbar. In another embodiment, the dimethyl fumarate is dried at a pressure of about 80 to about 100 mbar. In one embodiment, the dimethyl fumarate is dried for about 10 to about 100 hours, about 20 to about 90 hours, about 30 to about 80 hours, about 40 to about 80 hours, about 40 to about 70 hours, or about 46 to about 72 hours. In another embodiment, the dimethyl fumarate is dried for about 46 to about 48 hours.

Following the drying process, the dimethyl fumarate is processed further to obtain the desired particle size using conventional methods known in the art. The particles are reduced in size to produce particles of a suitable size for consistent handling for drug product processing. In one embodiment, the dimethyl fumarate is processed by jet milling. In one embodiment, the dimethyl fumarate is reduced to a particle size of less than 250 μm. In another embodiment, the dimethyl fumarate is reduced to a particle size from about 20 to about 1000 μm, about 40 to about 1000 μm, about 100 to about 1000 μm, about 200 to about 1000 μm, about 20 to about 750 μm, about 20 to about 250 μm, about 40 to about 750 μm, about 40 to about 250 μm, about 40 to about 100 μm, about 100 to about 750 μm, or about 100 to about 250 μm. In another embodiment, the dimethyl fumarate is reduced to a particle size wherein ≥97% of the particles have a particle size of ≤250 μm. In another embodiment, the dimethyl fumarate is reduced to a particle size wherein 90%, 92%, 95%, 97%, 98%, or 99% of the particles have a particle size of less than 250 μm.

The particle sizes reported here are based on a measured distribution. In one embodiment, the particle sizes are measured using a Laser Diffraction technique that correlates light scattering to particle volume on which "effective length or effective diameter" is calculated. The distribution is based on a measurement of thousands of particles. Particles samples can be in dry form or in slurry. In one embodiment, the instrument used to determine particle size/distribution is a Beckman Coulter LS230 or a Malvern Mastersizer.

In another embodiment, a fumarate can be reduced in size to produce particles of a suitable size for consistent handling from drug product processing. The fumarate can be, for example, a compound that converts to methyl hydrogen fumarate in vivo after administration. In one embodiment, only some of the fumarate present in a pharmaceutical composition is converted to methyl hydrogen fumarate in vivo. In one embodiment, the fumarate is dimethyl fumarate, monomethyl fumarate, fumaric acid, a salt of monomethyl fumarate, a salt of fumaric acid, or any combination thereof. In another embodiment, the fumarate can be a compound of formula (I):

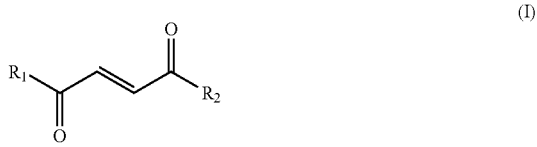

wherein $R_1$ and $R_2$ are independently OH, O$^-$, $C_1$-$C_6$ alkoxy, or a pharmaceutically acceptable salt thereof. The $C_1$-$C_6$ alkoxy can be chosen from, for example, $C_1$-$C_5$ alkoxy, $C_1$-$C_4$ alkoxy, $C_1$-$C_3$ alkoxy, $C_1$-$C_2$ alkoxy, $C_2$-$C_3$ alkoxy, $C_2$-$C_4$ alkoxy, $C_2$-$C_5$ alkoxy, or $C_2$-$C_6$ alkoxy and may be linear or branched. In still yet another embodiment, the fumarate is a dialkyl fumarate. In one embodiment, the fumarate is processed by jet milling. In one embodiment, the fumarate is reduced to a particle size of less than 250 μm. In another embodiment, the fumarate is reduced to a particle size from about 20 to about 1000 μm, about 40 to about 1000 μm, about 100 to about 1000 μm, about 200 to about 1000 μm, about 20 to about 750 μm, about 20 to about 250 μm, about 40 to about 750 μm, about 40 to about 250 μm, about 40 to about 100 μm, about 100 to about 750 μm, or about 100 to about 250 μm. In another embodiment, the fumarate is reduced to a particle size wherein ≥97% of the particles have a particle size of ≤250 μm. In another embodiment, the fumarate is reduced to a particle size wherein 90%, 92%, 95%, 97%, 98%, or 99% of the particles have a particle size of less than 250 μm.

In one aspect, the method produces a composition comprising the crystal form I of dimethyl fumarate. The composition can be substantially pure crystal form I. The single-crystal structure of dimethyl fumarate is disclosed in Kooijman, H., et al., *Acta Crystallographica* E60:o917-o918 (2004). The composition can be characterized by peaks in X-ray powder diffraction in degrees 2θ at 10.96° and 22.01°. The composition can be characterized by peaks in X-ray powder diffraction at 2θ of 10.96°, 22.01°, 24.07°, 24.11, 24.17, and 27.39. The composition can further include a pharmaceutically acceptable carrier.

Dimethyl fumarate in crystal form I can be prepared by recrystallization of crude dimethyl fumarate in a suitable solvent, such as acetone, anisole, benzyl alcohol, 1-butanol, 2-butanol, cumene, dichloromethane, diethyl ether, 1,4-dioxane, N,N-dimethylformamide (DMF), dimethyl sulfoxide (DMSO), ethyl acetate (EtOAc), ethanol, ethylene glycol, ethyl formate, water, heptane, isobutyl acetate, isopropyl ether, isopropyl acetate, isooctane, acetonitrile, methyl ethyl ketone, methanol, methyl acetate, methylcyclohexane, methyl isobutyl ketone, nitrobenzene, N-methylpyrrolidone (NMP), 1-octanol, isopentanol, propyl acetate, 1-propanol, 2-propanol, pyridine, t-butyl methyl ether (TBME), tetrahydrofuran (THF), triethylamine, trifluorotoluene, toluene, p-xylene, or mixtures thereof at a temperature suitable for dissolution of crude dimethyl fumarate. Alternatively, crude dimethyl fumarate can be dissolved in a mixture of a solvent, (e.g., THF, DMF, DMA, or NMP) and an antisolvent, such as water, methanol, ethanol, isopropyl alcohol, n-butyl alcohol, t-butyl methyl ether (TBME), acetone, acetonitrile, 1,2-dimethoxyethane, or a mixture thereof, at a temperature suitable for dissolution of crude dimethyl solvent. An antisolvent can then be added to the mixture under conditions suitable for the formation of crystal form I. For example crude dimethyl fumarate can be recrystallized in a mixture of heptane and ethyl acetate, a mixture of dichloromethane and methanol, a mixture of water and tetrahydrofuran, a mixture of acetone and water, a mixture of ethanol and water, or a mixture of methanol and water. In one embodiment, crude dimethyl fumarate is recrystallized in a 1:1 mixture of dichloromethane:methanol. In another embodiment, In one embodiment, crude dimethyl fumarate is recrystallized in an about 1:1, about 1:2, or about 2:1 mixture of dichloromethane:methanol. In another embodiment, crude dimethyl fumarate is recrystallized in an about 1:1, about 1:2, or about 2:1 mixture of water:tetrahydrofuran. In another embodiment, crude dimethyl fumarate is recrystallized in an about 1:1, about 1:2, about 1:3, or about 2:1 mixture of acetone:water. In another embodiment, crude dimethyl fumarate is recrystallized in an about 1:1, about 2:1, about 3:1, about 4:1, about 5:1, about 6:1, about 7:1, about 8:1, about 9:1, about 10:1, or about 1:2 mixture of ethanol:water. In another embodiment, crude dimethyl fumarate is recrystallized in an about 1:1, about 2:1, about 3:1, about 4:1, about 5:1, about 6:1, about 7:1, about 8:1, about 9:1, about 10:1, or about 1:2 mixture of methanol:water.

The high purity dimethyl fumarate has a low level of dimethyl sulfate. In one embodiment, the level of dimethyl sulfate is from about 0 to about 5 ppm, about 0 to about 4 ppm, about 0 to about 2 ppm, about 0.1 to about 5 ppm, about 0.1 to about 4.5 ppm, about 0.1 to about 4 ppm, about 0.1 to about 3 ppm, about 0.1 to about 2 ppm, about 0.5 to about 5 ppm, about 0.5 to about 4 ppm, about 0.5 to about 3 ppm, or about 0.5 to about 2 ppm. In another embodiment, the level of dimethyl sulfate is less than 5 ppm. In another embodiment, the level of dimethyl sulfate is less than 4.5 ppm. In another embodiment, the level of dimethyl sulfate is less than 4.0 ppm. In another embodiment, the level of dimethyl sulfate is less than 3.5 ppm. In another embodiment, the level of dimethyl sulfate is less than 3.0 ppm. In another embodiment, the level of dimethyl sulfate is less than 2.5 ppm. In another embodiment, the level of dimethyl sulfate is less than 2.0 ppm. In another embodiment, the level of dimethyl sulfate is less than 1.5 ppm. In another embodiment, the level of dimethyl sulfate is less than 1.0 ppm. In another embodiment, the level of dimethyl sulfate is less than 0.5 ppm. In another embodiment, the level of dimethyl sulfate is less than 0.1 ppm.

The level of dimethyl sulfate can be determined in the final product using conventional methods known in the art. In one embodiment, the level of dimethyl sulfate is determined by gas chromatography mass spectrometry (GC-MS).

Gas chromatography mass spectrometry could not be applied to the in-process samples that contained sulfuric acid, fumaric acid, and methanol. Attempts to use an orthogonal analytical method for dimethyl sulfate using the derivatizing agent, triethylamine, were investigated. However, it was found that dimethyl fumarate reacted with triethylamine producing a false positive result for dimethyl sulfate.

The reaction kinetics for the formation of methyl methanesulfonate has been measured using $^1$H NMR techniques (Teasdale, A., et al., Org. Proc. Res. Dev. 14:999-1007 (2010)). The application of similar $^1$H NMR techniques proved successful in determining the reaction kinetics for the formation of dimethyl sulfate during the reaction process. In one embodiment, the level of dimethyl sulfate is measured during the reaction process using $^1$H NMR.

Using $^1$H NMR it was possible to study the formation and fate of monomethyl sulfate (MMS) and dimethyl sulfate (DMS) for the esterification of fumaric acid using methanol and sulfuric acid. Dimethyl sulfate is known to be a genotoxin and its reactivity as an electrophile methylating agent in $S_N2$ reactions is greater than that of methyl iodide (F. K. Thayer, J. Am. Chem. Soc. 46:1044-1046 (1924)). Conversely, monomethyl sulfate is a poor alkylating agent and is not genotoxic. The potential formation of DMS as an impurity in the reaction was investigated.

Commercial DMS manufacture is typically performed with $SO_3$ and anhydrous methanol catalyzed by Pd or other transition metals (F. K. Thayer, J. Am. Chem. Soc. 46:1044-1046 (1924)). These forcing conditions are quite different from the gentle refluxing of $H_2SO_4$ in methanol during the esterification process.

A multi-step reaction mechanism was proposed for the generation and consumption of monomethyl sulfate and dimethyl sulfate as shown in Scheme 2 (Teasdale, A., et al., Org. Proc. Res. Dev. 14:999-1007 (2010)).

Scheme 2

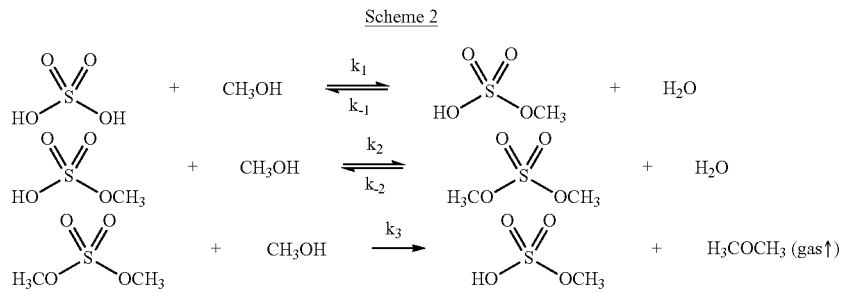

In contrast to previously studied alkyl sulfonic acids (such as methane and ethane sulfonic acids), sulfuric acid can undergo two sequential reactions with methanol to generate different sulfate esters. Monomethyl sulfate is a relatively benign nongenotoxic impurity that can be controlled like other process-related contaminants (see An, J., et al., J. Pharm. Biomed. Anal. 48: 1006-1010 (2008); Zhenga, J., et al., J. Pharm. Biomed. Anal. 50:1054-1059 (2009); Alzaga, R., et al., J. Pharm. Biomed. Anal. 45:472-479 (2007)). In contrast, DMS is a known genotoxic impurity and must be controlled to very low levels (1.5 ug/day) (D. I. Robinson, Org. Proc. Res. Dev. 14:946-959 (2010)). It was important to examine the formation and fate of these two sulfate esters under actual process conditions to fully understand the potential process risk presented by DMS.

Formation of Monomethyl Sulfate ($k_1$)

The formation of MMS is depicted in Scheme 3.

Scheme 3

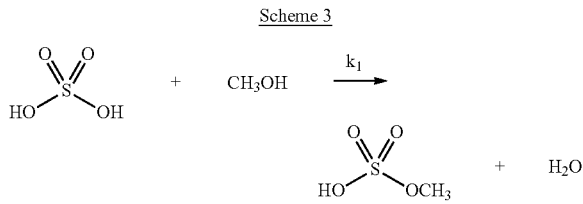

Hydrolysis of Monomethyl Sulfate ($k_{-1}$)

Monomethyl sulfate can either hydrolyze back to sulfuric acid ($k_{-1}$) or further react with methanol to form DMS ($k_2$). The hydrolysis of MMS is presented in Scheme 4.

Scheme 4

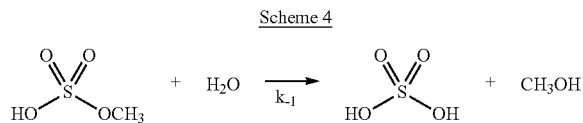

Methanolysis and Hydrolysis of Dimethyl Sulfate

Dimethyl sulfate is formed and consumed in a complex set of interrelated equilibria. Rates of DMS solvolysis (methanolysis and hydrolysis) can be readily measured, and these are the pathways by which DMS is consumed. However, the amount of DMS that is formed by the forward reaction between methanol and MMS is very small. Hence, to simplify the experimental design we first measured the DMS methanolysis (Scheme 5) and hydrolysis rates (Scheme 6). The equilibrium level of remaining dimethyl sulfate following methanolysis was then used to derive the forward rate of formation for DMS.

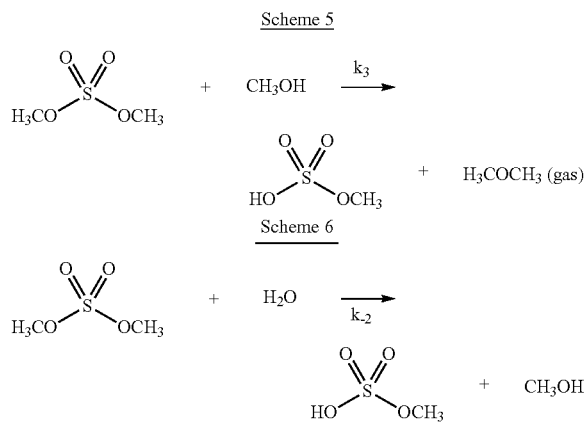

Formation of Dimethyl Sulfate ($k_2$)

The formation of DMS from MMS is shown in Scheme 7.

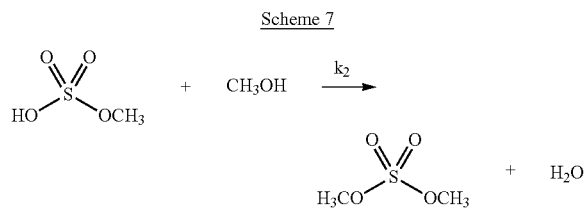

The forward reaction rate for DMS ($k_2$) can be calculated under steady-state conditions (d[DMS]/dt=0) as follows:
a. at equilibrium, the rate of formation and loss of DMS are in balance, and:

$$d[DMS]/dt=0=k_2[MMS][CH_3OH]-k_{-2}[DMS][H_2O]-k_3[DMS][CH_3OH]$$

b. solving for $k_2$:

$$k_2=(k_{-2}[DMS][H_2O]+k_3[CH_3OH])/[MMS][CH_3OH]$$

c. If the equilibrium is reached under dry conditions, the equation can be further simplified:

$$k_2=k_3[DMS][CH_3OH]/[MMS][CH_3OH]=k_3[DMS]/[MMS]$$

Thus, the rate constant for the formation of DMS ($k_2$) can be calculated if [DMS] can be measured once at equilibrium since $k_3$, [MMS], and [CH$_3$OH] are known.

The compound can be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides, and iodides, aralkyl halides, such as benzyl and phenethyl bromides and others. Water or oil-soluble or dispersible products are thereby obtained.

The compound can be formulated into pharmaceutical compositions that can be administered orally, parenterally, by inhalation spray, topically, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional, and intracranial injection or infusion techniques.

Pharmaceutical compositions can include dimethyl fumarate, or pharmaceutically acceptable derivatives thereof, together with any pharmaceutically acceptable carrier. The term "carrier" as used herein includes acceptable adjuvants and vehicles. Pharmaceutically acceptable carriers that can be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The pharmaceutical compositions can be in the form of a sterile injectable preparation, for example a sterile injectable aqueous or oleaginous suspension. This suspension can be formulated according to techniques known in the art using suitable dispersing or wetting agents and suspending agents. The sterile injectable preparation can also be a sterile injectable solution or suspension in a non-toxic parenterally-acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions can also contain a long-chain alcohol diluent or dispersant.

The pharmaceutical compositions can be orally administered in any orally acceptable dosage form including, but not limited to, capsules, tablets, aqueous suspensions or solutions.

In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents can also be added.

Alternatively, the pharmaceutical compositions can be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For topical applications, the pharmaceutical compositions can be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions can be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions can be formulated in an ointment such as petrolatum.

The pharmaceutical compositions can also be administered by nasal aerosol or inhalation through the use of a nebulizer, a dry powder inhaler or a metered dose inhaler. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

The amount of active ingredient that can be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient can also depend upon the therapeutic or prophylactic agent, if any, with which the ingredient is co-administered.

In some embodiments, the dimethyl fumarate, crystal form I of dimethyl fumarate, or combinations thereof can be administered in an amount ranging from about 1 mg/kg to about 50 mg/kg (e.g., from about 2.5 mg/kg to about 20 mg/kg or from about 2.5 mg/kg to about 15 mg/kg). The amount of dimethyl fumarate, crystal form I of dimethyl fumarate, or combinations thereof administered will also vary, as recognized by those skilled in the art, dependent on route of administration, excipient usage, and the possibility of co-usage with other therapeutic treatments including use of other therapeutic agents.

For example, the dimethyl fumarate, crystal form I of dimethyl fumarate, or combinations thereof can be administered to a subject, for example orally, in an amount of from about 0.1 g to about 1 g per day, or for example, in an amount of from about 100 mg to about 800 mg per day. The dimethyl fumarate, crystal form I of dimethyl fumarate, or combinations thereof can be administered, for example, in an amount of from about 120 mg per day to about 240 mg per day, from about 120 mg per day to about 480 mg per day, or from about 120 mg per day to about 720 mg per day.

For example, 720 mg of the dimethyl fumarate, crystal form I of dimethyl fumarate, or combinations thereof per day may be administered in separate administrations of 2, 3, 4, 5 or 6 equal doses (e.g., 3 equal doses). For example, 480 mg of the dimethyl fumarate, crystal form I of dimethyl fumarate, or combinations thereof per day may be administered as a single daily dose of 480 mg or as 2 daily dosages of 240 mg each. If the 480 mg of the dimethyl fumarate, crystal form I of dimethyl fumarate, or combinations thereof is administered in 2 daily doses, each dose can consist of (1) 2 tablets containing 120 mg for a total dose of 240 mg or (2) 1 tablet containing 240 mg.

EXAMPLES

Having now generally described this invention, the same will be understood by reference to the following examples which are provided herein for purposes of illustration only and are not intended to be limiting unless otherwise specified.

Example 1

Method A

Preparation of Dimethyl Fumarate

In a 100 mL stirred jacketed reactor with reflux condenser was added fumaric acid (17.3 g; 149 mmol) followed by methanol (100 mL). The slurry was stirred under ambient temperature and sulfuric acid (3.66 g; 37.3 mmol) was added. The reaction mixture was then heated to 65° C. and held at that temperature for approximately 3 hours. The reaction solution was then cooled to <20° C. in 3-8 hours during which the product precipitated. The product was filtered and the cake washed with 2×20 mL methanol. The wet cake was dried under vacuum at 20-30° C. to yield dry dimethyl fumarate (16 g).

Example 2

Method B

Preparation of Dimethyl Fumarate

In a 100 mL stirred jacketed reactor with reflux condenser was added 7 g (60.3 mmol) of fumaric acid, methanol (50 mL), and 2.25 g (17.7 mmol) oxalyl chloride. The mixture was heated to 65° C. and held for 2 hours. The solution was then cooled to 20° C. in 8 hours. The product filtered and washed with methanol (30 mL). The wet cake was dried under vacuum at 20-30° C. to yield 6.9 g of dimethyl fumarate.

Example 3

Method C

Preparation of Dimethyl Fumarate

In a 100 mL stirred jacketed reactor with reflux condenser was added 17.3 g (149 mmol) of fumaric acid, 2 g of Amberlyst resin, and methanol (100 mL). The mixture was heated to 65° C. and held for 24 hours followed by hot filtration to remove the resin and additional 40 mL methanol rinse. The slurry was reheated to 65° C. and slowly cooled to 20° C. The product was filtered and washed using 2×15 mL methanol, and dried to yield 9.1 g dimethyl fumarate.

Example 4

Esterification of Fumaric Acid

Fumaric acid (161.5 (1391 mol) to 162.5 kg (1400 mol)) was added to a 1000 L glass-lined reactor followed by the addition of 740 to 742 kg methanol. The slurry mixture was stirred at approximately 100 RPM and the reaction initiated by the addition of 34.5 to 35.0 kg of sulfuric acid to the vessel.

The mixture was heated to reflux at 60-70° C. for at least 3 hours. At this point in the esterification reaction, less than 10% methyl hydrogen fumarate was present in the reaction mixture. The hot mixture was then transferred under inert nitrogen to the crystallizer to crystallize the dimethyl fumarate as described in Example 5. The process gave 147 kg (1019 moles, 73% yield) of dry dimethyl fumarate prior to milling. The milling process provided 143 kg (991 moles, 97% yield) of milled dimethyl fumarate. The overall yield for the entire process from fumaric acid to milled drug substance was 71%.

Normal operating ranges are provided in Table 1.

TABLE 1

Esterification Reaction Parameters.

| Parameter | Proven Acceptable Range | Normal Operating Range |
| --- | --- | --- |
| Methanol (reagent/solvent) | 5.7-8.6 (L/kg FA) | 5.77-5.81 (L/kg FA) |
| Fumaric acid (FA), batch size (kg) (starting material) | 140-181 kg | 161.5-162.5 kg |
| Sulfuric acid (catalyst) | 0.01-0.5 equiv. | 0.238-0.243 equiv. |
| Reaction Temperature | 60-70° C. | 60-70° C. |
| Time to desired (equilibrium) conversion | 1.5-48 h | 3-27 h |
| Amount of water in starting material: | 2-5% total | |
| MeOH | ≤0.5% | ≤0.1% |
| Fumaric acid | ≤0.5% | ≤0.5% |

The formation of dimethyl fumarate was analyzed under varying sulfuric acid amounts as shown in FIG. 1. Reaction using normal operating conditions with different amount of sulfuric acid catalyst (0.01, 0.05, and 0.25 mol. equivalent) provided dimethyl fumarate in similar isolated yields (78-79%) with no detectable amount of methyl hydrogen fumarate. The reaction profiles (constructed from Fourier Transform Infrared Spectroscopy and normalized to the final concentration measured by High-performance liquid chromatography) suggest that equilibrium concentrations of product were achieved at all levels of sulfuric acid catalyst used if the reaction was held for a sufficiently long period of time.

Example 5

Crystallization of Dimethyl Fumarate

Dimethyl fumarate was crystallized by cooling the final reaction mixture of Example 4. Crystallization studies suggested that the rate of cooling does not affect product purity, particle size and yield. The dimethyl fumarate crystals nucleate at around 58-60° C. and are mostly out of solution at 40-45° C. In the current process the mixture was cooled from reaction temperature 65° C. to the end temperature 20-25° C. in about 8 hours, stirred for 1-2 hours, and filtered to isolate the product.

Table 2 highlights results from laboratory crystallization experiments with cooling rates chosen within manufacturing equipment capabilities. As shown in Table 2, the cooling rate has no impact on product purity, mean particle size, and isolated yield.

TABLE 2

Results of Lab Crystallization Experiments with Different Cooling Rates.

| Cooling Rate | Purity | Mean Particle Size[1] | Isolated Yield |
| --- | --- | --- | --- |
| 5° C./h | 99.97% | 475 μm | 85% |
| 8° C./h | 99.97% | 448 μm | 84% |
| 15° C./h | 99.97% | 475 μm | 83% |

[1]Mean particle size in this table refers to the dimethyl fumarate isolated from the reaction mixture prior to milling.

Other process parameters that were examined include agitation power (rate), final end temperature, and stirring time at crystallization end temperature. Variation in these parameters had minimal effects on product attributes (including purity, particle size, and yield). The ranges studied for cooling rate, agitation power (rate), hold time, and end temperature are provided in Table 3 along with the normal operating ranges used in the manufacturing process.

TABLE 3

Crystallization Process Parameters.

| Parameter | Proven Acceptable Range | Normal Operating Range |
| --- | --- | --- |
| Cooling rate | 2-15° C./h | 5-5.6° C./h |
| Agitation power | 0.7 W/kg-3 W/kg | 1.4-2.3 W/kg (*) |
| Hold period at end temperature | 1-6 hours | 1-2 hours |
| End Temperature | 0 -25° C. | 20-25° C. |

(*) At manufacturing scale 1.4-2.3 W/kg corresponds to 100-120 rpm.

Example 6

Isolation of Dimethyl Fumarate

The dimethyl fumarate product of Example 5 was filtered using a centrifuge. The wet cake contained about 5% of the mother liquor that contained methanol, methyl hydrogen fumarate, fumaric acid, and sulfuric acid. This mother liquor was displaced by methanol during cake washing under ambient conditions. The total amount of methanol wash used in the current manufacturing process was 368 kg (~2.5 kg MeOH/kg product).

The parameters examined in development studies were cake height/thickness and amount of methanol wash. Variation in cake height/thickness during manufacture is expected due to splitting of the batch in 4 portions to accommodate for centrifuge capacity.

Lab studies with varying amounts of methanol wash has shown a wide range of wash volumes produce dimethyl fumarate with acceptable product quality even using ratios as low as 0.66 kg methyl alcohol per kg product. The isolation step with methanol cake wash is considered robust and the normal recommended wash ranges provide a 2-9 fold performance operating margin.

Normal operating ranges for cake height/thickness and amount of methanol wash are provided in Table 4.

TABLE 4

Cake Washing Process Parameters.

| Parameter | Proven Acceptable Range | Normal Operating Range |
|---|---|---|
| Cake height/thickness* | 2-12 cm | 2-12 cm (16-64 kg wet cake) |
| Total amount of methanol wash | 0.66-6.49 kg MeOH/kg product | 1.44-5.75 kg MeOH/kg product |

*calculated based on centrifuge diameter and weight of the wet cake per load.

Example 7

Drying of Dimethyl Fumarate

The extent of drying of the dimethyl fumarate isolated in Example 6 depends on time, temperature, and to some extent the type and capacity of dryer. For the current 162 kg batch scale the drying time using a dryer listed in Table 5 could last for as long as 72 hours. An In-Process-Check (IPC) was performed at 48 hours to determine methanol and water levels and drying was subsequently stopped if a satisfactory level <0.15% for methanol and <0.10% for water was achieved. In the future this IPC can be omitted and drying can be terminated at a pre-determined time based on specific dryer used.

The effect of temperature, pressure, and drying time on particle size was also investigated. Dimethyl fumarate has a low measurable vapor pressure and therefore placing the material under reduced pressure in a dryer could potentially promote sublimation and subsequent particle size changes. Development studies examined the extent of sublimation under the drying conditions employed in the manufacturing plant. The comparison of particle size obtained from different drying time in the laboratory and plant dryer is presented in Table 5. The first 3 entries in Table 5 are lab samples collected after 7, 24, and 48 hours drying time. The result from the three lab samples confirms that drying has no effects on the particle size. The particle size of lab samples were also compared to two representative plant samples which were dried for 48 hours and 72 hours. There is no change in particle size during drying.

TABLE 5

Similarity of dimethyl fumarate particle size during and after drying.

| | Drying | Particle Size (µm) by Laser Diffraction | | | | |
|---|---|---|---|---|---|---|
| Entry | Time | Mean | D10 | D50 | D90 | D97 |
| 1 | 7 h (lab) | 524 | 328 | 566 | 850 | 987 |
| 2 | 24 h (lab) | 521 | 323 | 562 | 843 | 979 |
| 3 | 48 h (lab) | 535 | 340 | 567 | 845 | 980 |
| 4 | 48 h (plant) | 536 | 332 | 561 | 828 | 956 |
| 5 | 72 h (plant) | 524 | 327 | 562 | 834 | 963 |

Normal operating ranges for temperature, pressure, and drying time are provided in Table 6.

TABLE 6

Drying Process Parameters.

| Parameter | Proven Acceptable Range | Normal Operating Range |
|---|---|---|
| Temperature | 20-35° C. | 23-27° C. |
| Pressure | 30-100 mbar | 80-100 mbar |
| Time | 46-72 h | 46-48 h |

Example 8

Particle Size Reduction of Dimethyl Fumarate

The dried dimethyl fumarate of Example 7 was processed further in a jet mill. These particles were milled to produce particles of a suitable size for consistent handling and uniformity for drug product processing. The target specification for particle size is ≥97% of the particles <250 µm. The dimethyl fumarate drug substance was milled consistently to meet this specification using a jet mill. The proven acceptable and normal operating ranges are listed in Table 7.

TABLE 7

Particle Size Reduction Parameters

| Parameter | Proven Acceptable Range | Normal Operating Range |
|---|---|---|
| Feed rate | 192-204 kg/h | 198 ± 2.4 kg/h |
| Mill Pressure (venturi and grind) | 7-8 bar | 7.6 ± 0.2 bar |

The mean particle size of the dimethyl fumarate isolated from the dryer (~550-650 µm) of Example 7 was reduced after milling to around 20-40 µm and was acceptable for use in the drug product process. It is evident that the milling operation is capable of producing a drug substance of suitable quality.

Example 9

Recrystallization of Dimethyl Fumarate

Crystals were obtained by sublimation (Staples, R. J. and Gingold, J. A., *Z. Kristallogr. NCS* 224:121-123 (2009)) of a small amount of material. A colorless block crystal with dimensions 0.24×0.16×0.11 mm was mounted on a Nylon loop using a very small amount of paratone oil.

Data were collected using a Bruker CCD (charge coupled device) based diffractometer equipped with an Oxford Cryostream low-temperature apparatus operating at 173 K. Data were measured using omega and phi scans of 0.5° per frame for 30 s. The total number of images was based on results from the program COSMO (COSMO V1.56, *Software for the CCD Detector Systems for Determining Data Collection Parameters*. Bruker Analytical X-ray Systems, Madison, Wis. (2006)) where redundancy was expected to be 4.0 and completeness to 100% out to 0.83 Å. Cell parameters were retrieved using APEX II software (APEX2 V 1.2-0 *Software for the CCD Detector System*; Bruker Analytical X-ray Systems, Madison, Wis. (2006)) and refined using SAINT on all observed reflections. Data reduction was performed using, the SAINT software (SAINT V 7.34 *Software for the Integration of CCD Detector System* Bruker Analytical X-ray Systems, Madison, Wis. (2001)) which corrects for Lp (Lorentz-polarization factor). Scaling and absorption corrections were applied using SADABS (SADABS V2.10 Program for *absorption corrections using Bruker-AXS CCD based on the method of Robert Blessing*; Blessing, R. H. *Acta Cryst. A*51, 1995, 33-38) multi-scan technique. The structures are solved by the direct method using the SHELXS-97 program and refined by least squares method on $F^2$, SHELXL-97, which are incorporated in SHELXTL-PC V 6.10 (Sheldrick, G. M., *Acta Cryst. A*64:112-122 (2008)).

The structure was solved in the space group $P_1$. All non-hydrogen atoms are refined anisotropically. Hydrogens were calculated by geometrical methods and refined as a riding model. The crystal used for the diffraction study showed no decomposition during data collection. All drawings are done at 50% ellipsoids.

TABLE 8

Crystal data and structure refinement for crystal form I of dimethyl fumarate.

| | |
|---|---|
| Empirical formula | C6 H8 O4 |
| Formula weight | 144.12 |
| Temperature | 173(2) K |
| Wavelength | 1.54178 Å |
| Crystal system | Triclinic |
| Space group | P -1 |
| Unit cell dimensions | a = 3.87380(10) Å   α = 100.851(2)° |
| | b = 5.6502(2) Å    β = 100.1910(10)° |
| | c = 8.3774(2) Å    γ = 105.860(2)° |
| Volume | 168.091(8) Å³ |
| Z | 1 |
| Density (calculated) | 1.424 Mg/m³ |
| Absorption coefficient | 1.047 mm$^{-1}$ |
| F(000) | 76 |
| Crystal size | 0.24 × 0.16 × 0.11 mm³ |
| Theta range for data collection | 5.54 to 67.75°. |
| Index ranges | -4 <= h <= 4, -5 <= k <= 6, -9 <= l <= 10 |
| Reflections collected | 2275 |
| Independent reflections | 586 [R(int) = 0.0334] |
| Completeness to theta = 67.75° | 96.2% |
| Absorption correction | Semi-empirical from equivalents |
| Max. and min. transmission | 0.7530 and 0.4904 |
| Refinement method | Full-matrix least-squares on $F^2$ |
| Data/restraints/parameters | 586/0/48 |
| Goodness-of-fit on $F^2$ | 1.142 |
| Final R indices [I > 2sigma(I)] | R1 = 0.0442, wR2 = 0.1094 |
| R indices (all data) | R1 = 0.0449, wR2 = 0.1105 |
| Extinction coefficient | 0.55(5) |
| Largest diff. peak and hole | 0.235 and -0.272 e.Å$^{-3}$ |

TABLE 9

Atomic coordinates (×10⁴) and equivalent isotropic displacement parameters (Å² × 10³) for crystal form I of dimethyl fumarate. U(eq) is defined as one third of the trace of the orthogonalized $U^{ij}$ tensor.

| | x | y | z | U(eq) |
|---|---|---|---|---|
| O(1) | 2940(3) | 5310(2) | 1948(1) | 27(1) |
| O(2) | -686(3) | 2229(2) | 2812(1) | 38(1) |
| C(1) | 3075(4) | 7126(3) | 3450(2) | 29(1) |
| C(2) | 944(3) | 2912(3) | 1797(2) | 23(1) |
| C(3) | 991(4) | 1215(3) | 221(2) | 24(1) |

TABLE 10

Bond lengths [Å] and angles [°] for crystal form I of dimethyl fumarate.

| | |
|---|---|
| O(1)—C(2) | 1.3331(17) |
| O(1)—C(1) | 1.4494(16) |
| O(2)—C(2) | 1.2045(17) |
| C(1)—H(1A) | 0.9800 |
| C(1)—H(1B) | 0.9800 |
| C(1)—H(1C) | 0.9800 |
| C(2)—C(3) | 1.4850(19) |
| C(3)—C(3)#1 | 1.320(3) |
| C(3)—H(3) | 0.9500 |
| C(2)—O(1)—C(1) | 115.57(11) |
| O(1)—C(1)—H(1A) | 109.5 |
| O(1)—C(I)—H(1B) | 109.5 |
| H(1A)—C(1)—H(1B) | 109.5 |
| O(1)—C(1)—H(1C) | 109.5 |
| H(1A)—C(1)—H(1C) | 109.5 |
| H(1B)—C(1)—H(1C) | 109.5 |
| O(2)—C(2)—O(1) | 124.03(13) |
| O(2)—C(2)—C(3) | 124.76(13) |
| O(1)—C(2)—C(3) | 111.21(12) |
| C(3)#1—C(3)—C(2) | 121.04(16) |
| C(3)#1—C(3)—H(3) | 119.5 |
| C(2)—C(3)—H(3) | 119.5 |

Symmetry transformations used to generate equivalent atoms: #1 -x, -y, -z

TABLE 11

Anisotropic displacement parameters (Å² × 10³) for crystal form I of dimethyl fumarate. The anisotropic displacement factor exponent takes the form: $-2\pi^2[h^2\ a^{*2}\ U^{11} + \ldots + 2\ h\ k\ a^*\ b^*\ U^{12}]$

| | $U^{11}$ | $U^{22}$ | $U^{33}$ | $U^{23}$ | $U^{13}$ | $U^{12}$ |
|---|---|---|---|---|---|---|
| O(1) | 31(1) | 19(1) | 28(1) | 4(1) | 12(1) | 3(1) |
| O(2) | 48(1) | 27(1) | 34(1) | 4(1) | 23(1) | -1(1) |
| C(1) | 33(1) | 21(1) | 30(1) | 1(1) | 10(1) | 6(1) |
| C(2) | 21(1) | 21(1) | 26(1) | 7(1) | 7(1) | 4(1) |
| C(3) | 24(1) | 24(1) | 25(1) | 8(1) | 9(1) | 7(1) |

TABLE 11

Hydrogen coordinates (×10⁴) and isotropic displacement parameters (Å² × 10³) for crystal form I of dimethyl fumarate.

| | x | y | z | U(eq) |
|---|---|---|---|---|
| H(1A) | 557 | 7102 | 3499 | 44 |
| H(1B) | 4533 | 8831 | 3429 | 44 |
| H(1C) | 4225 | 6671 | 4437 | 44 |
| H(3) | 2471 | 1887 | -480 | 29 |

Examples 10-14

The following reaction conditions apply to Examples 10-14:

All $^1$H NMR spectra were obtained in and referenced against DMSO-$d_6$ at 2.5 ppm using a Varian 500 MHz NMR. Concentrated sulfuric acid, fumaric acid, and dimethyl fumarate were obtained from the Sigma-Aldrich Chemical Company. Authentic standards of MMS (Na salt) and DMS were also obtained from Sigma-Aldrich. For spiking identification purposes, an authentic sample of MMS was prepared by passing a methanolic solution of the commercially available sodium salt through Amberlite FPA 22 resin (H form, 10 molar equivalents), and concentrating to an oil on a flash evaporator.

All small scale reactions performed in the study were magnetically stirred and carried out using an insulated oil bath maintained at 65 deg±1° C. Methanol used in this study contained no more than 0.01% water, and was further dried using 3 Å Zeolite molecular sieves that had been predried overnight at 175° C. Concentrated sulfuric acid purchased from Sigma-Aldrich was >99.9% nominal purity, and was used as provided.

Sampling of reactions involved removal of a minimum of 150-400 μL of reaction solution, addition to DMSO-$d_6$ (lock solvent) as required to make up a 650 μL solution in each NMR tube. Samples were chilled in an ice/water bath, and analyzed within 5-10 minutes of their preparation. Reaction profiles were tracked by plotting reaction completion (via reactant integral measurements) against time.

Although DMS was present in only trace amount upon reaching equilibrium following extended methanolysis, the S/N ratio of the DMS peak was >10:1 and thus could be measured with confidence. However, the MMS and its left satellite peak (nearby in chemical shift to the DMS resonance) could not be accurately integrated electronically due to the baseline deflections in this region from the broad methyl resonance of MeOH (solvent). As a result, the spectrum was enlarged and the peaks physically extracted and weighed in order to obtain the molar ratio. The error associated with this measurement procedure was expected to be no more than 10% and comparable to other sources of experimental and computational uncertainties.

Fitting of all experimental data to generate rate constant data and an overall kinetic model was carried out using DynoChem (version 3.3).

GC-MS Extraction Method for DMS Analysis in the Process Solutions: Agilent 6890N GC; Supelco Equity-1701 (30 m×0.32 mm, 1.0 m) column with Helium carrier gas at 2 ml/min (constant flow); FID Detector; thermal gradient from 50° C. to 280° C. over 21 minutes. Weigh ~100 mg of sample into a 10 mL conical tube, add 10.0 mL of 0.1M NaCl to the sample tube and vortex. Add 1.0 mL of methyl t-butyl ether (MBTE). Cap, vortex, then agitate for 5 minutes. Centrifuge at 4000 rpm for 10 minutes. Remove 200 μL of MTBE top layer, put into vial, analyze by GC.

DMS spiking experiment. In order to learn about the effect of large amount of spiked DMS on the DMS level of API, 0.55% (5500 ppm) of DMS (relative to API) was added to the reaction mixture (100 gram batch) at the start of the reaction. The following conditions were used for this spiking experiment:
1. Charge 100 g of dicarboxylic acid starting material.
2. Charge 580 mL of MeOH and start agitation at 480 rpm.
3. Charge 21.3 g of sulfuric acid
4. Heat the reaction to 67° C.
5. Charge DMS (0.55% wt/wt (5500 ppm) relative to the resulting API).
6. Maintain at this temperature for 3 hrs. Remove aliquot for analysis during 3 h reaction time.
7. Cool to 22° C. in 8 hr and hold for 2 hr.
8. Filter and wash cake four times with 70 mL of MeOH.
9. Dry the cake at 22° C. at 100 mmHg.
10. Sample dry API for DMS content,

Example 10

Formation of Monomethyl Sulfate

Dry methanol (<0.01% water) was mixed with concentrated dry sulfuric acid and heated to 65° C. After waiting a minute to reach 65° C., $^1$H NMR (16 transients) were collected for seven discrete samples. Data collection for this entire set of samples occurred within 12 minutes. Equilibrium was reached within 1 hour, resulting in an essentially quantitative conversion of sulfuric acid to monomethyl sulfate. The heated sample remained unchanged after several days' storage in a sealed tube. The identity of the MMS resonance in the NMR spectrum was confirmed by spiking an authentic sample of monomethyl sulfate into the reaction mixture. The MMS peak integral (C$\underline{H}_3$, 3.45 ppm) was normalized to the methyl peak resonance of the MeOH solvent (C$\underline{H}_3$, 3.18 ppm) and DynoChem version 3.3 was used to calculate the forward rate constant ($k_1$) from the peak integral data. The study was conducted twice with good agreement between the two derived rate constants. The second-order forward rate constant ($k_1$) for the formation of MMS at 65° C. was determined to be $6.4 \times 10^{-5}$ L/mol-sec with a confidence interval of ±7% RSD.

Example 11

Hydrolysis of Monomethyl Sulfate

The rate constant of this reaction was measured by spiking water into solutions containing MMS (1.5 mole %) and monitoring the heated, sealed, vessel by $^1$H NMR for 45 hours. Water was spiked into the matrix at two different levels—6 mole % and 12 mole %. In both cases, the MMS level remained virtually unchanged confirming that the equilibrium for this reaction lies far to the right. In order to develop the larger model, the MMS equilibrium constant K ($k_1/k_{-1}$) was assigned a value of 999:1 in favor of the forward reaction, thus conservatively defining $k_{-1}$ as $6.4 \times 10^{-8}$ L/mol-sec.

In related work, Wolfenden and Yuan, P.N.A.S. 104:83-86 (2007) measured the rate constants for the hydrolysis of MMS over a range of temperatures and pH and found the extrapolated values (at 25° C.) to be $1.7 \times 10^{-8}$ M$^{-1}$ s$^{-1}$ (1M HCl, T=40° C. to 100° C.) and $2.2 \times 10^{-11}$ M$^{-1}$ s$^{-1}$ (pH=3 to 10, T=100° C. to 190° C.). In addition they also measured the equilibrium constant for the hydrolysis of monomethyl sulfate across a range of temperatures (T=100° C. to 150° C.) and sulfuric acid concentrations (1-4 M) and found the rate to be fairly constant at 0.027 M$^{-1}$. Results from both labs confirm that MMS is formed rapidly, and it is stable under over a wide range of temperatures and water concentrations. These results are also consistent with the fact that monomethyl sulfuric acid is a poor alkylating agent.

Example 12

Methanolysis of Dimethyl Sulfate

Solutions of 1.5 mole % DMS and methanol were heated in a sealed tube to 35° C. and the time-dependent NMR spectra were collected for these mixtures. Data obtained over 60 minutes showed that dimethyl ether (DME) and MMS resonances gradually increased with time with a concurrent decline in DMS. Use of NMR data helped confirm the reaction mechanism proposed in Scheme 2.

The reaction proceeded more slowly at 35° C. but clearly confirms the formation of dimethyl ether (DME). The gradual downfield shift of the exchangeable OH resonance (4.8 ppm) supports the generation of a strong acid i.e., MMS (Scheme 5). Another set of duplicate experiments were performed under the reaction conditions at 65° C. (again spiking 1.5 mole % DMS into dry methanol with <0.01% water and no sulfuric acid) and monitoring the reaction for 60 minutes. This reaction was considered to be essentially irreversible under nominal plant process conditions since the reaction vessels are not pressurized and the resultant dimethyl ether would bubble out of solution.

The rate constant for the methanolysis of DMS ($k_3$) was derived from this data using DynoChem and found to be $4.1 \times 10^{-5}$ L/mol-sec.

Example 13

Hydrolysis of Dimethyl Sulfate

The hydrolysis rate of dimethyl sulfate was determined by spiking known amounts of water into a mixture of DMS and methanol. Water was spiked into DMS-methanol solutions at three different levels—10.5, 14.0, and 17.7 mole % equivalents. The reactions were monitored for 60 minutes at 65° C. and the DMS peak integrals obtained.

The rate constant for the hydrolysis of DMS ($k_{-2}$) was derived by fitting all the data to a DynoChem model that used the time-dependant peak integral data. The experimentally determined value for $k_{-2}$ was found to be $2.3 \times 10^{-4}$ L/mol-sec (see Kolensikov, V. A., *Kinetika I Katliz* 18:1065-1066 (1977) and Chan, L. C., et al., *Org. Proc. Res. Dev.* 12:213-217 (2008)).

The profiles of the DMS methanolysis and hydrolysis experiments revealed that MMS was formed more rapidly when the MeOH solution contained water. Conversely, dimethylether formation was retarded by the addition of water. These results suggest a bimolecular mechanism for DMS methanolysis ($k_3$) and hydrolysis ($k_{-2}$). Methanol and water compete to consume the available DMS in an $S_N^2$-like displacement reaction. Despite being at a low concentration relative to methanol, the more nucleophilic water molecule is able to hydrolyze DMS more quickly than dimethyl sulfate can react with MeOH ($k_{-2} > k_3$).

Teasdale, A., et al., *Org. Proc. Res. Dev.* 14:999-1007 (2010) disclosed similar findings in their study of the methanolysis and hydrolysis of methyl methane sulfonate. Their investigation using $O^{18}$ labeled methanol confirmed that oxygen in the dimethyl ether, formed during methanolysis of methyl methane sulfonate, came from methanol and not methane sulfonic acid.

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications, and publications cited herein are incorporated by reference in their entirety.

What is claimed is:

1. A method for the preparation of dimethyl fumarate, which comprises:
reacting:
(a) fumaric acid; and
(b) methanol;
in the presence of sulfuric acid; in a ratio of methanol to fumaric acid of about 5.7 to about 8.6 liters of methanol per kilogram of fumaric acid;
in a reaction mixture to obtain a product mixture comprising dimethyl fumarate and dimethyl sulfate, wherein the level of dimethyl sulfate is less than 4.0 ppm.

2. The method of claim 1, wherein the level of dimethyl sulfate is less than 3.0 ppm.

3. The method of claim 1, wherein the level of dimethyl sulfate is less than 2.0 ppm.

4. The method of claim 1, wherein the level of dimethyl sulfate is less than 1.0 ppm.

5. The method of claim 1, further comprising:
reducing the particle size of the dimethyl fumarate.

6. The method of claim 5, wherein the reduced particle size of dimethyl fumarate ranges from about 20 μm to about 250 μm.

7. The method of claim 1, wherein the ratio of fumaric acid:sulfuric acid is in a range from about 1:0.01 to about 1:0.50 molar equivalents.

8. The method of claim 1, wherein the reacting is for about 3.0 to about 48 hours.

9. The method of claim 1, wherein the reacting occurs at a temperature of from about 60° C. to about 70° C.

10. The method of claim 1,
wherein the ratio of fumaric acid:sulfuric acid is in a range from about 1:0.01 to about 1:0.50 molar equivalents,
the reaction mixture further comprises about 2.0% to about 5.0% water,
the reacting is for about 3.0 to about 48 hours, and
the reacting occurs at a temperature of from about 60° C. to about 70° C.

11. The method of claim 2, wherein the ratio of fumaric acid:sulfuric acid is in a range from about 1:0.01 to about 1:0.50 molar equivalents.

12. The method of claim 2, wherein the reacting is for about 3.0 to about 48 hours.

13. The method of claim 2, wherein the reacting occurs at a temperature of from about 60° C. to about 70° C.

14. The method of claim 2,
wherein the ratio of fumaric acid:sulfuric acid is in a range from about 1:0.01 to about 1:0.50 molar equivalents,
the reaction mixture further comprises about 2.0% to about 5.0% water,
the reacting is for about 3.0 to about 48 hours, and
the reacting occurs at a temperature of from about 60° C. to about 70° C.

15. The method of claim 3, wherein the ratio of fumaric acid:sulfuric acid is in a range from about 1:0.01 to about 1:0.50 molar equivalents.

16. The method of claim 3, wherein the reacting is for about 3.0 to about 48 hours.

17. The method of claim 3, wherein the reacting occurs at a temperature of from about 60° C. to about 70° C.

18. The method of claim 3,
wherein the ratio of fumaric acid:sulfuric acid is in a range from about 1:0.01 to about 1:0.50 molar equivalents,
the reaction mixture further comprises about 2.0% to about 5.0% water,
the reacting is for about 3.0 to about 48 hours, and
the reacting occurs at a temperature of from about 60° C. to about 70° C.

19. The method of claim 4, wherein the ratio of fumaric acid:sulfuric acid is in a range from about 1:0.01 to about 1:0.50 molar equivalents.

20. The method of claim 4, wherein the reacting is for about 3.0 to about 48 hours.

21. The method of claim 4, wherein the reacting occurs at a temperature of from about 60° C. to about 70° C.

22. The method of claim 4,
wherein the ratio of fumaric acid:sulfuric acid is in a range from about 1:0.01 to about 1:0.50 molar equivalents,
the reaction mixture further comprises about 2.0% to about 5.0% water,
the reacting is for about 3.0 to about 48 hours, and
the reacting occurs at a temperature of from about 60° C. to about 70° C.

23. The method of claim 1, wherein the reaction mixture further comprises about 2.0% to about 5.0% water.

24. The method of claim 2, wherein the reaction mixture further comprises about 2.0% to about 5.0% water.

25. The method of claim 3, wherein the reaction mixture further comprises about 2.0% to about 5.0% water.

26. The method of claim 4, wherein the reaction mixture further comprises about 2.0% to about 5.0% water.

27. The method of claim 1, wherein the dimethyl fumarate is crystal form I of dimethyl fumarate.

28. The method of claim 22, wherein the dimethyl fumarate is crystal form I of dimethyl fumarate.

\* \* \* \* \*